(12) United States Patent
Lange et al.

(10) Patent No.: US 7,238,206 B2
(45) Date of Patent: Jul. 3, 2007

(54) FUSION IMPLANT

(75) Inventors: Robert Lange, Paris (FR); Armand Linge, Richterswil (SE); Steve Olson, Knoxville, TN (US)

(73) Assignee: Co-Ligne AG, Zurich (CH)

( * ) Notice: Subject to any disclaimer, the term of this patent is extended or adjusted under 35 U.S.C. 154(b) by 0 days.

(21) Appl. No.: 10/960,073

(22) Filed: Oct. 8, 2004

(65) Prior Publication Data

US 2005/0085914 A1   Apr. 21, 2005

(30) Foreign Application Priority Data

Oct. 17, 2003   (EP)   .................... 03405751

(51) Int. Cl.
   *A61F 2/44*   (2006.01)
(52) U.S. Cl. .................................. 623/17.11
(58) Field of Classification Search ........ 623/17.11–16
   See application file for complete search history.

(56) References Cited

U.S. PATENT DOCUMENTS

| | | | | |
|---|---|---|---|---|
| 3,867,728 A | * | 2/1975 | Stubstad et al. | 623/17.16 |
| 5,108,438 A | * | 4/1992 | Stone | 623/17.16 |
| 5,192,327 A | | 3/1993 | Brantigan | |
| 5,306,310 A | | 4/1994 | Siebels | |
| 5,571,189 A | * | 11/1996 | Kuslich | 623/17.12 |
| 6,022,376 A | * | 2/2000 | Assell et al. | 623/17.16 |
| 6,159,211 A | | 12/2000 | Boriani et al. | |
| 6,187,043 B1 | * | 2/2001 | Ledergerber | 623/8 |
| 6,245,108 B1 | | 6/2001 | Biscup | |
| 6,527,805 B2 | * | 3/2003 | Studer et al. | 623/17.16 |
| 6,712,853 B2 | * | 3/2004 | Kuslich | 623/17.16 |
| 6,726,721 B2 | * | 4/2004 | Stoy et al. | 623/17.16 |
| 6,733,531 B1 | * | 5/2004 | Trieu | 623/17.11 |
| 6,733,533 B1 | * | 5/2004 | Lozier | 623/17.12 |
| 6,783,546 B2 | * | 8/2004 | Zucherman et al. | 623/17.16 |
| 2001/0014826 A1 | | 8/2001 | Biedermann et al. | |
| 2002/0123750 A1 | * | 9/2002 | Eisermann et al. | 606/69 |
| 2004/0049270 A1 | * | 3/2004 | Gewirtz | 623/17.11 |

FOREIGN PATENT DOCUMENTS

| | | |
|---|---|---|
| EP | 0 517 030 A | 12/1992 |
| EP | 1 236 451 A | 9/2002 |
| WO | WO 02/076316 A1 | 10/2002 |

* cited by examiner

*Primary Examiner*—Eduardo C. Robert
*Assistant Examiner*—Annette Reimers
(74) *Attorney, Agent, or Firm*—Sughrue Mion, PLLC

(57) ABSTRACT

A fusion implant apparatus, in for the replacement of a vertebra or an intervertebral disc, having at least one biocompatible structure. The structure is made of a composite material having reinforcing fibers, and has a first and second face to engage adjacent bone structures to be fused, struts extending between the first and second faces, and a hollow interior space for reception of bone growth inducing substances. The fibers are long fibers and the majority of these long fibers have a direction that follows the longitudinal forces upon the first and second faces, which is the direction of trabecular structures of the adjacent bone structure, so that a majority of long fibers are essentially an extension of these trabecular structures.

17 Claims, 3 Drawing Sheets

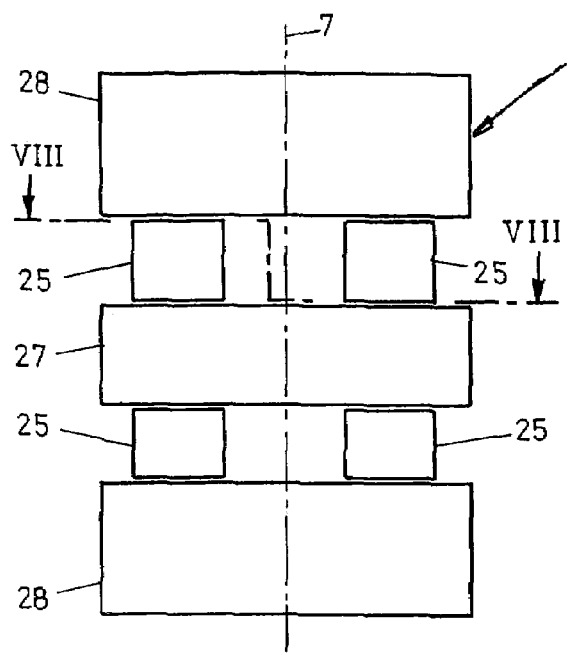
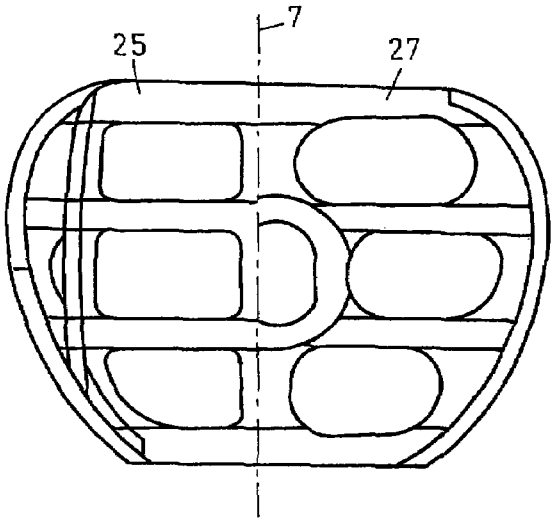
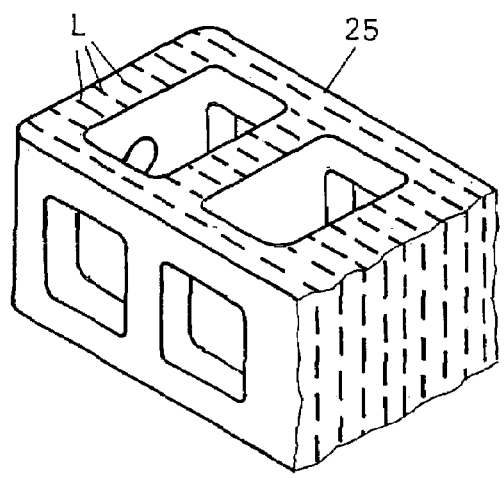
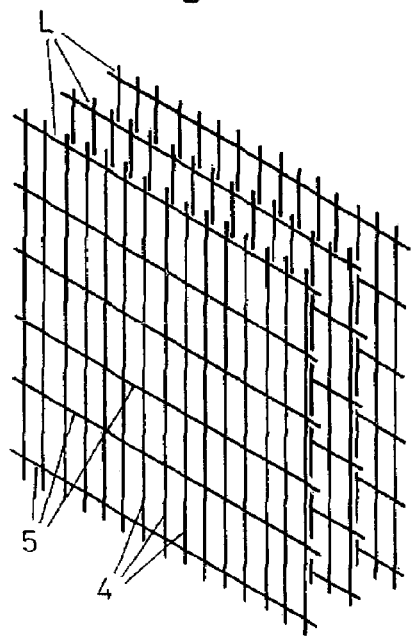

FUSION IMPLANT

BACKGROUND

The present invention relates to a fusion implant, in particular for the replacement of a vertebra or an intervertebral disk, which comprises a biocompatible material having reinforcing fibers.

U.S. patent application 2001/0014826 A1 describes a space holder for a vertebra or an intervertebral disc. It comprises a jacket made of titanium and having a first and second edge to engage adjacent bone structures to be fused. Titanium implants like this can resist the load and provide initial stability. They meet the short term requirements, but not all mid and long term requirements. In particular they do not assure maximum bone fusion from one healthy bone structure to the other and they inhibit certain radiological assessments and therapies.

U.S. Pat. No. 5,306,310 discloses a prothesis as a vertebral replacement element that is tubular and made of helical strands of carbon fiber reinforced composite material. The fibers are running in the longitudinal direction of the strands.

U.S. Pat. No. 5,192,327 discloses implants stackable together to allow variability of ultimate implant height. The implants are made of a radiolucent carbon fiber reinforced polymer.

EP 1 236 451 discloses a medical implant made of fiber reinforced plastic, wherein the fibers are oriented in relationship of the biochemical requirements to obtain the appropriate strength and stiffness.

WO 02/076316 discloses a modular implant for fusing adjacent bone structure. It is made of ring-like segments and has an internal cavity for the reception of bone growth inducing substances.

There are, therefore, fusion implants available, which can be easily assembled, inserted and secured to replace a vertebra or an intervertebral disc and which bear the load normally carried by vertebral structure, which have been removed. These implants mostly fulfill the short term requirements.

The purpose of a spinal fusion is for two vertebra to grow together and form one healthy bridge of bone, which regenerates itself through the natural physiological process over time. This is achieved by placing bone generating substances between two healthy vertebra and holding them in place with anchors, such as screws, rods and plates. Interbody devices exist to hold the bone generating substances, but also to serve s a mechanical strut during the healing and bridging process.

Inert stability of the fixation and therefore the short term requirement is the major goal, if the patient cannot expect to live very long. But patients today live longer and expect to remain active. Tumor or fracture patients can expect to live for decades and return to a normal life. Fusion implants must therefore last up to sixty years. Yet, any inert device, whether it is metal, plastic or composite will wear out over time and if overstressed, fracture. On the other hand, a living and healthy bone bridge will continue to rebuild itself for the rest of the patient's life. A fusion implant should therefore not only provide initial support for corrected bone, but also enhance the generation of a stable bone bridge between the adjacent bone structures to be fused. That will track natural vertebrae functions as closely as possible.

It is an object of the present invention to provide a fusion implant that not only meets the short term requirements of stability, the mid term requirements of bone healing but also the long term mechanical requirements to assure the structural regeneration of bone. According to the invention a fusion implant made of composite material having reinforcing fibers is provided, wherein the fibers are long fibers and wherein the majority of these long fibers have a direction that follows the longitudinal forces upon said first and second faces, which is the direction of trabecular structures of the adjacent bone structures, so that said majority of long fibers are an extension of these trabecular structure. The implant according to the present invention is able to mimic the complex structure of a bone structure and in particular a vertebra and therefore imitate the mechanical properties for site-specific bone regeneration. The majority of the long fibers are oriented in a longitudinal axis, which is head to toe according to the site specific stress, in the same direction as the trabecular alignment of the vertebral body. These fibers are in fact an extension of these trabecula.

The invention considers the following properties of bone:
a) Bone is anisotropic
b) Bone regenerates itself through the patient's life according to the stress upon it
c) Bone without stress resorbs and looses its density and ability to resist stress and bear load or disappears all together.

An inert mechanical implant wears through fatigue over time. Living bone, like other tissues, when properly stressed, regenerates and strengthen over time.

The fusion implant according to the present invention provides not only the specific mechanical resistance to allow stability, but through orientation of the fibers better achieves the site specific anisotropic properties of a bone required to maintain it healthy. The implant replicates the micro movement or contortion and the site specific, anisotropic mechanical qualities of the vertebrae. It is stiffer and stronger in one direction than another, according to the specific requirements of load bearing bone the implant must replace.

The trabeculars of the bone are regenerated and oriented according to the stress received. As the trabeculars demonstrate the complex multi-directional forces the bone receives, these can be used to orient the long fibers.

The implant as described herein not only replicates the outer anatomical form of the bone structure to be replaced, but also its inner mechanical structure to imitate the performance of the surrounding tissue. The implants are not only strong enough to resist collapse, but are also flexible enough to better propagate forces through the surrounding bone, which promotes bone healing and regeneration.

Composite material containing long fibers is uniquely suited to work with bone for the generation of new bone and remodeling. A remolding occurs, when the vascular support remains intact and the bone begins to bear load. The new bone tissues recognize the forces of the load and lay down trabecula. Trabecula are beams or planks in the support structure of a bone and are oriented according to the load they receive. Trabecula receiving load are reinforced and those that do not are weakened or removed. With the implant according to the present invention the new bone growth can be stressed as it transfers stress with the proper orientation of long fibers. The implant is flexible enough so that it will not unduly isolate stresses from the bone growth material as is the case with the known stable but stiff implants. It is just as strong as known implants but is able to transmit stress to the bone within the component because of its limited and controlled flexibility.

The invention permits the manufacture of an assembly of two or more biocompatible structures that allows a lordotic curve. Such an assembly allows to curve the orientation of the fibers and to mate with the orientation of the predominant weight bearing trabeculars.

Other advantages and features of the present invention will be apparent to those skilled in the art after reading the following specification with references to the accompanying drawings.

BRIEF DESCRIPTION OF THE DRAWINGS

FIG. 7 is a diagrammatic view of an alternative implant of the invention FIG. 8 is a sectional view along the line VIII—VIII of FIG. 7, FIG. 9 is a perspective view of a stackable biocompatible structure of the implant of FIG. 7 with parts in section and broken away to show the manner in which the fibers are predominantly oriented and FIG. 10 a diagrammatic view to show the fibers arranged in parallel layers and the predominantly orientation of the fibers.

DESCRIPTION OF THE PREFERRED EMBODIMENTS

Figure 1:
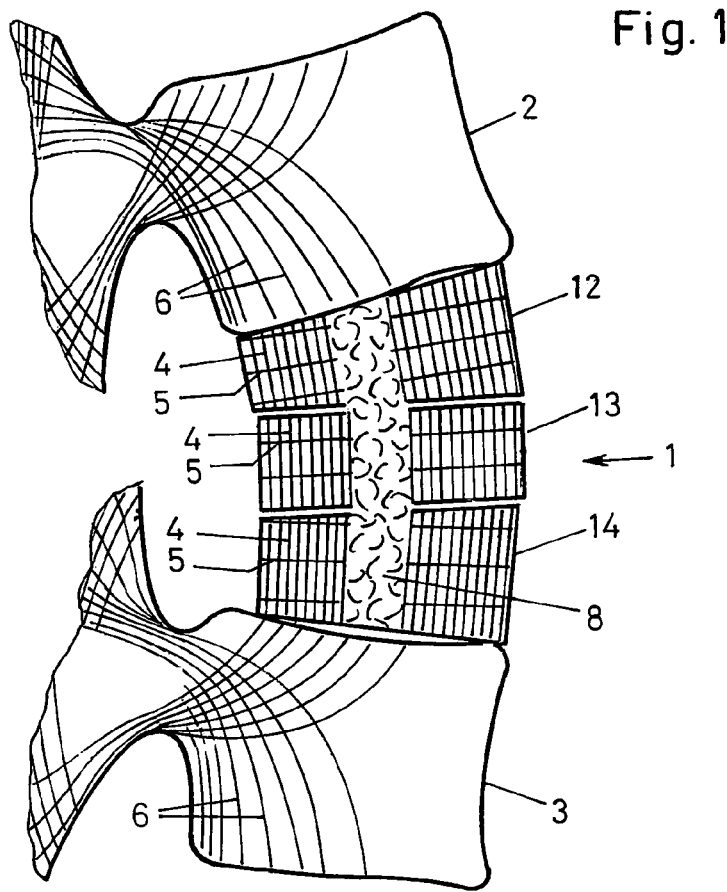
FIG. 1 is a section view of the implant of FIG. 2.
Figure 2:
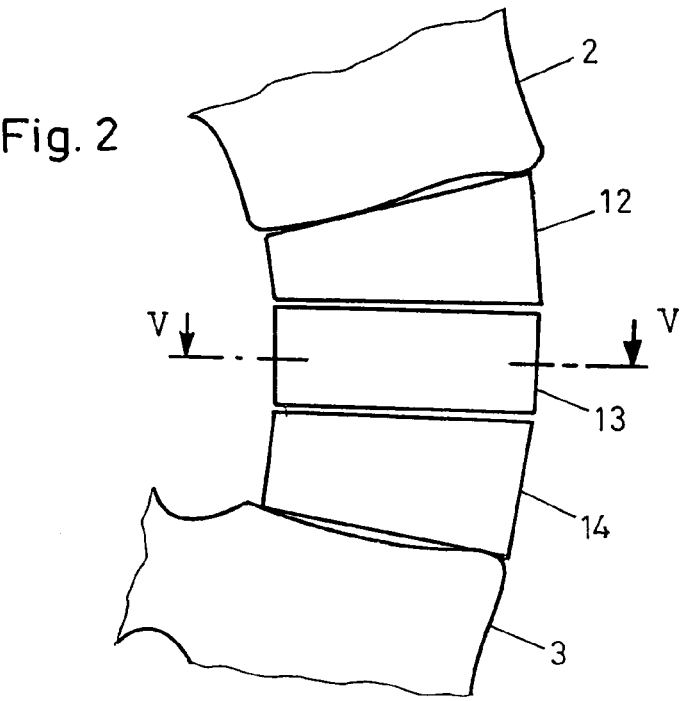
FIG. 2 is a side view of an implant of this invention showing the implant inserted between two vertebrae.
Figure 5:
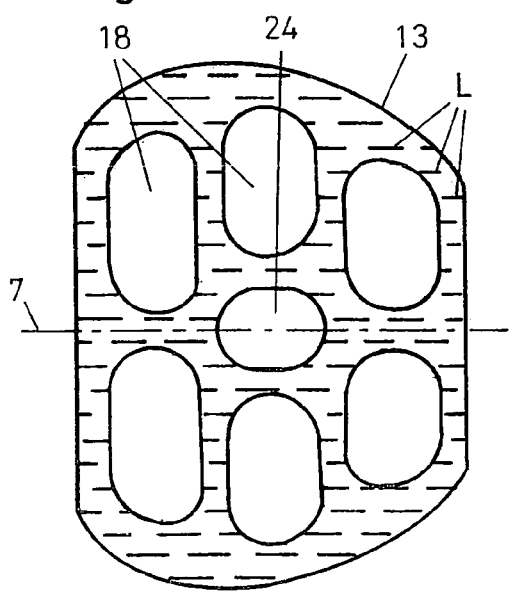
FIG. 5 is a sectional view along the line V—V of FIG. 2.
Figure 6:
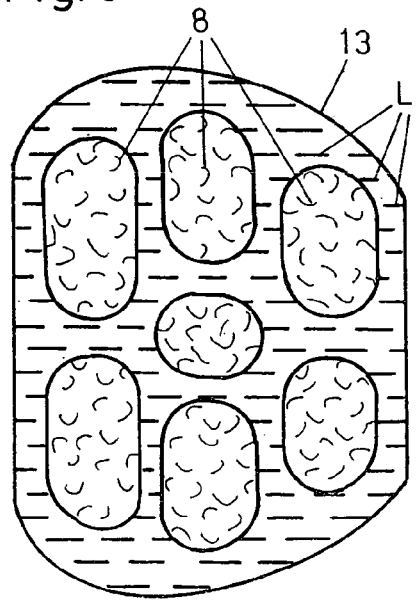
FIG. 6 is a sectional view according to FIG. 5 but with an alternative orientation of the fibers.

FIGS. 1 and 2 show a vertebral implant 1, that comprises three cages 12, 13 and 14, which are arranged between two vertebrae 2 and 3. The implant 1 allows total removal and replacement of a vertebrae. The cages 12, 13 and 14 are constructed of predominate fibers 4 and secondary fibers 5, which are embedded in a matrix, preferably made of PEEK or PEKEKK. The fibers 4 and 5 are assembled in wafers or layers L, which are parallel to the sagittal plane or midline 7, as indicated in FIG. 5.

The cages 12, 13 and 14 have each a top 16 and a bottom 17 and openings 18 as well as struts 19, which divide the cages in compartments. The openings 18 are filled with bone graft or bone fragments 8 which will grow and join the vertebrae 2 and 3 together as though they were a single unit.

The predominate fibers 4 and the secondary fibers 5 are oriented according to the trabecula 6 as illustrated in FIG. 1. The secondary fibers 5 act as a brace and are oriented perpendicular to the predominated fibers 4 and in the anterior posterior direction as illustrated in FIGS. 1 and 10. The secondary fibers 5 resist the complex moment in the anterior and posterior direction that comes from bending and flexing backward. This resists more force and moment in the anterior posterior direction and produces a micro movement under anatomic loads that will be closer to the bone implant 1 replaces. As the fibers 4 and 5 are oriented according to the trabecula 6, the implant 1 has an anisotropic structure that moves more like a normal bone.

The implant 1, when subject to the complex stresses and moment, experiences both compression and tension. The structural fibers 4 and 5 therefore compress and distract as it moves. The bone graft 8 inside the implant 1 is subject to the same compression and tension, which is site specific and therefore remodels to bear and resist these forces. Through the orientation of the fibers 4 and 5 under stress and moment replicates site specific micro movements, the compression and distraction of the vertebrae 2 and 3. This micro movement subjects the newly incorporated bone graft 8 to the proper forces and therefore manages the remodeling process according to a specific site. Over time, the trabecula lay themselves down according to the forces they bear and this allows the forces to rebuild over time.

The implant 1 as illustrated in FIGS. 1 and 2 is a superstructure that stacks the fibers 4 and the struts 19 as well as the openings 18 level upon level at angels according to the bending orientation of the long running trabecula 6. By stacking interdigiting struts 19 in the dominant plane of load, a quasi-bend of the fibers is achieved. The quasi-bend structure of the implant 1 better replicates the micro movement of a longer bone. It therefore helps the trabecula to remodel according to the forces that remodeled bone must one day bear. Such a quality is most valuable in longer structures, where more bone is removed and then must be remade.

Figure 3:
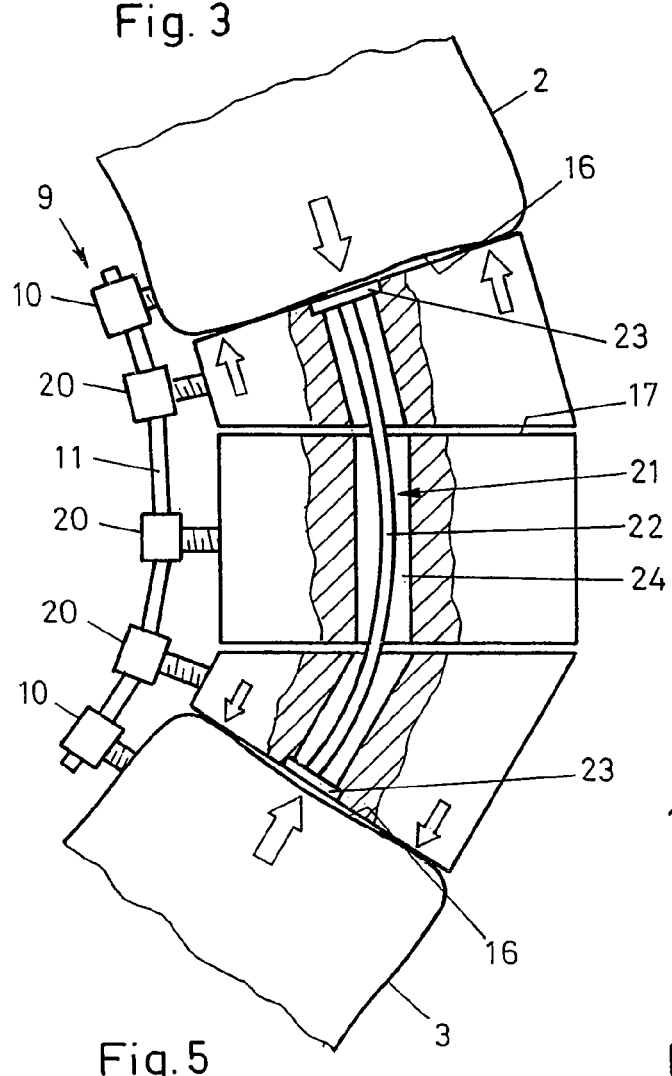
FIG. 3 is a partial section view of the implant of FIG. 2 showing the fixation and compression of the three parts.
Figure 4:
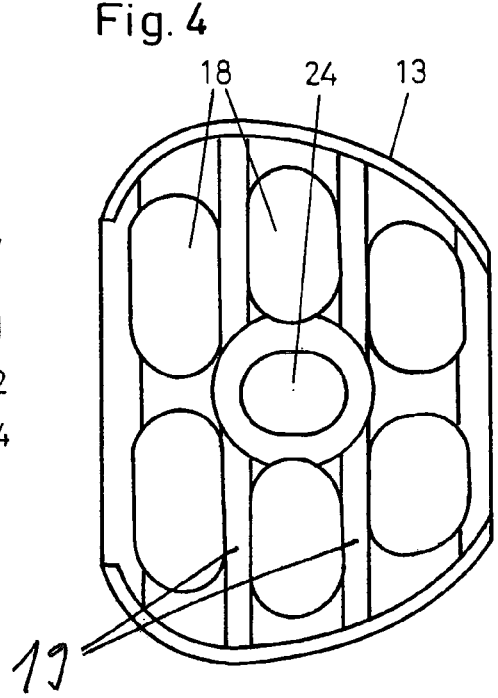
FIG. 4 is a top view of an implant of this invention.

The cages 12, 13 and 14 are held in place with a fixation system 9 which comprises pedicle screws 10, plates or rods 11 and anchors 20 which connect the cages 12, 13 and 14 with the plates or rods 11. As illustrated in FIG. 3, the cages 12, 13 ad 14 are compressed together with a compression device 21, which comprises a bolt 22 and nuts 23. The bending compression device 21 holds the implant 1 together and allows the quasi-bending of the implant. As illustrated in FIG. 3, the compression device 21 is arranged in a channel 23 that is located within the implant 1. The fixation system 9 as well as the compression device 21 are preferably made of radiolucent material in order to allow the attending physician to observe postoperative progress accurately.

FIGS. 7 and 8 show an implant 1' according to another embodiment of the invention. The implant 1' is also a superstructure that stacks the fibers and struts as explained above. It contains hemi components or cages 25 which are arranged in a distance to each other. Between two cages 25 of the same level there is additional space 26 for bone graft not shown. The cages 25 are fixed between cages 27 and 28 which contain fibers as explained above. The fibers embedded in the hemi cages 25 are assembled in layers L which are parallel to the sagittal plane 7. The same applies to the fibers embedded in the cages 27 and 28. The implant 1' can be curved as shown in FIGS. 1 and 2.

List of Reference Numbers
1 Implant 16 Top
2 Vertebra 17 Bottom
3 Vertebra 18 Opening
4 predominate fibers 19 Struts
5 secondary fibers 20 Compression device
6 trabecula 21 Bolt
7 sagittal plane or midline 22 Nut
8 Bone graft 23 Channel
9 Fixation system 24 Channel
10 Screw (pedicle screw) 25 Cage
11 Rod 26 Space
12 Cage 27 Cage
13 Cage 28 Cage
14 Cage L Layers
15 Top

The invention claimed is:

1. A fusion implant apparatus, for the replacement of a vertebra or an intervertebral disc, that is anisotropic like normal bone, comprising:

at least one biocompatible structure, wherein said structure is made of a composite material having reinforcing fibers, said structure having a first and second face to engage adjacent bone structures to be fused, struts, which divide the biocompatible structure into compartments, extending between said first and second faces and a hollow interior space for reception of bone growth inducing substances, wherein the fibers are long fibers and wherein the majority of these long fibers are oriented in parallel to a longitudinal axis and have a direction that follows the longitudinal forces upon said first and second faces, which is the direction of trabecular structures of the adjacent bone structure, so that said majority of long fibers are essentially an extension of these trabecular structures, and are both (1) oriented according to the trabecular of the vertebra to be fused and (2) oriented in the anterior posterior direction, wherein said majority of long fibers are braced with further long fibers oriented essentially perpendicular to said majority of long fibers.

2. A fusion implant according to claim 1, wherein at least two biocompatible structures engage one another and which define in communication an internal cavity for reception of said bone growth substances.

3. A fusion implant according to claim 2, wherein each of said biocompatible structures contains a majority of long fibers which are extensions of said trabecular structures.

4. A fusion implant according to claim 1, wherein said long fibers are encapsulated in a polymer matrix.

5. A fusion implant according to claim 1, wherein at least 60% of the fibers have a direction that follows said longitudinal forces.

6. A fusion implant according to claim 1, wherein at least two biocompatible structures are stacked together.

7. A fusion implant according to claim 6, wherein at least one biocompatible implant is tapered to be thicker at its anterior end than at its posterior end.

8. A fusion implant according to claim 6, wherein a least two biocompatible structures replace a hemi-vertebra and at least one biocompatible structure replaces a full vertebra.

9. A fusion implant according to claim 8, wherein there is a space between the hemivertebral structures to receive bone growth inducing substances.

10. A fusion implant according to claim 6, wherein the biocompatible structures which are held in place with anchors, such as screws, rods and plates.

11. A fusion implant according to claim 1, wherein the fibers are assembled in layers , which are parallel to the sagittal plane or midline.

12. A fusion implant according to claim 1, wherein the implant is a bent superstructure made of at least two cages stacked together.

13. A fusion implant according to claim 12, wherein the cages are compressed together with a compression device.

14. A fusion implant according to claim 13 wherein the compression device allows a bending of the implant.

15. A fusion implant according to claim 13 or 14, wherein the compression device comprises a bolt arranged within a channel that is located within the implant.

16. A fusion implant according to claim 12, wherein the compression device comprises nuts and at least one bolt.

17. A fusion implant according to claim 1, wherein it contains at least two hemi cages arranged between two other cages.

\* \* \* \* \*